US012064379B2

United States Patent
Bellows et al.

(10) Patent No.: US 12,064,379 B2
(45) Date of Patent: Aug. 20, 2024

(54) MOUNTING PLATE FOR MEDICAL DEVICE SUSPENSION SYSTEM

(71) Applicant: American Sterilizer Company, Mentor, OH (US)

(72) Inventors: Lance Clark Bellows, Painesville, OH (US); Michael Joseph Heser, Willoughby, OH (US)

(73) Assignee: American Sterilizer Company, Mentor, OH (US)

( * ) Notice: Subject to any disclaimer, the term of this patent is extended or adjusted under 35 U.S.C. 154(b) by 679 days.

(21) Appl. No.: 16/797,326

(22) Filed: Feb. 21, 2020

(65) Prior Publication Data
US 2020/0268476 A1 Aug. 27, 2020

Related U.S. Application Data

(60) Provisional application No. 62/809,173, filed on Feb. 22, 2019.

(51) Int. Cl.
*A61G 12/00* (2006.01)
*F16M 13/02* (2006.01)

(52) U.S. Cl.
CPC ......... *A61G 12/004* (2013.01); *F16M 13/027* (2013.01)

(58) Field of Classification Search
CPC ......... A61B 50/28; A61B 90/35; A61B 90/50; F16M 9/00; F16M 13/00; F16M 13/02; F16M 13/027; A61G 12/004
(Continued)

(56) References Cited

U.S. PATENT DOCUMENTS

| | | | | |
|---|---|---|---|---|
| 6,095,468 A | * | 8/2000 | Chirico | F16M 11/2014 248/125.7 |
| 6,364,268 B1 | | 4/2002 | Metelski | |

(Continued)

FOREIGN PATENT DOCUMENTS

| | | |
|---|---|---|
| WO | 0145627 A1 | 6/2001 |
| WO | 03040609 A1 | 5/2003 |

(Continued)

OTHER PUBLICATIONS

PCT/US2020/019189; PCT International Search Report and Written Opinion of the International Searching Authority dated Jun. 11, 2020.

(Continued)

*Primary Examiner* — Jonathan Liu
*Assistant Examiner* — Guang H Guan
(74) *Attorney, Agent, or Firm* — Renner, Otto, Boisselle & Sklar, LLP

(57) ABSTRACT

A mounting plate for a medical device support system includes opposed major surfaces in a thickness direction. A group of plate mounting orifices is arranged in a hexagon pattern and extends through the opposed major surfaces and defines a perimeter of an area at the major surfaces. A primary orifice extends through the opposed major surfaces, and a group of primary spindle mounting orifices surround the primary orifice and extend through the opposed major surfaces, the primary orifice and the primary spindle mounting orifices located within the defined area. An auxiliary orifice extends through the opposed major surfaces and a group of auxiliary spindle mounting orifices surrounds the auxiliary orifice and extend through the opposed major surfaces, the group of auxiliary spindle mounting orifices defining a perimeter of an auxiliary spindle mounting area at
(Continued)

the major surfaces, one of the plate mounting orifices located within the auxiliary spindle mounting area.

15 Claims, 12 Drawing Sheets

(58) Field of Classification Search
USPC .................................................. 248/317, 343
See application file for complete search history.

(56) References Cited

U.S. PATENT DOCUMENTS

| | | | |
|---|---|---|---|
| 6,431,515 B1 | 8/2002 | Gampe et al. | |
| 6,443,412 B1 | 9/2002 | Kuhn | |
| 6,471,363 B2 | 10/2002 | Howell et al. | |
| 6,531,656 B1 * | 3/2003 | Grote | F16L 39/00 174/491 |
| 6,639,623 B2 | 10/2003 | Howell et al. | |
| 6,659,415 B2 | 12/2003 | Kummerfeld et al. | |
| 6,698,704 B2 | 3/2004 | Kuhn | |
| 6,817,585 B2 | 11/2004 | Wagner et al. | |
| 6,899,442 B2 | 5/2005 | Howell et al. | |
| 7,097,145 B2 | 8/2006 | Turner | |
| 7,191,992 B2 | 3/2007 | Wagner et al. | |
| 7,628,367 B2 * | 12/2009 | Friederich | F16M 11/2021 248/343 |
| 7,921,489 B2 | 4/2011 | Newkirk et al. | |
| 7,971,409 B2 * | 7/2011 | Bak et al. | E04B 1/2612 52/696 |
| 8,322,674 B2 | 12/2012 | Metelski | |
| 8,905,204 B2 | 12/2014 | Chandan et al. | |
| 8,960,624 B2 | 2/2015 | Szkola et al. | |
| 9,605,800 B2 * | 3/2017 | Huang | B65B 55/00 |
| 9,827,636 B2 * | 11/2017 | Tsui | B23K 37/0536 |
| 9,857,024 B1 * | 1/2018 | Culpepper | F16M 13/02 |
| 9,999,480 B2 | 6/2018 | Oginski et al. | |
| 10,398,528 B2 * | 9/2019 | Tao | F16C 19/16 |
| 10,656,341 B2 * | 5/2020 | Boccoleri | H04N 5/655 |
| 10,695,250 B2 * | 6/2020 | Tao | F16M 11/2014 |
| 10,835,346 B2 * | 11/2020 | Bellows | F16D 49/08 |
| 10,966,796 B2 * | 4/2021 | Bellows | A61B 90/30 |
| 10,993,778 B2 * | 5/2021 | Bellows | F16D 65/065 |
| D922,177 S * | 6/2021 | Pride | D8/349 |
| D945,606 S * | 3/2022 | Bellows | D24/128 |
| 11,275,293 B2 * | 3/2022 | Park | F16M 11/08 |
| 11,660,161 B2 * | 5/2023 | Bellows | A61B 90/50 606/1 |
| 11,732,841 B2 * | 8/2023 | Reavill | A61G 12/004 248/60 |
| 2002/0015296 A1 | 2/2002 | Howell et al. | |
| 2003/0021107 A1 | 1/2003 | Howell et al. | |
| 2003/0160142 A1 | 8/2003 | Brahler et al. | |
| 2005/0242261 A1 | 11/2005 | Brahler et al. | |
| 2006/0102811 A1 | 5/2006 | Musset et al. | |
| 2011/0147563 A1 | 6/2011 | Metelski | |
| 2012/0268565 A1 | 10/2012 | Guilleminot | |
| 2014/0131526 A1 | 5/2014 | Borg et al. | |
| 2017/0079743 A1 | 3/2017 | Tao et al. | |
| 2018/0259122 A1 * | 9/2018 | Reavill | A61B 90/35 |
| 2018/0372270 A1 | 12/2018 | Ravalitera et al. | |
| 2020/0268476 A1 * | 8/2020 | Bellows | A61G 12/004 |
| 2020/0306006 A1 * | 10/2020 | Bellows | A61B 90/50 |
| 2023/0120143 A1 * | 4/2023 | Pichler | A61B 90/50 248/274.1 |
| 2024/0044447 A1 * | 2/2024 | Reavill | F16M 13/027 |

FOREIGN PATENT DOCUMENTS

| | | |
|---|---|---|
| WO | 03072994 A2 | 9/2003 |
| WO | 2008112675 A1 | 9/2008 |
| WO | 2017125677 A1 | 7/2017 |

OTHER PUBLICATIONS

International Preliminary Report on Patentability for related International Application No. PCT/US2020/019189 mailed Feb. 1, 2021.

* cited by examiner

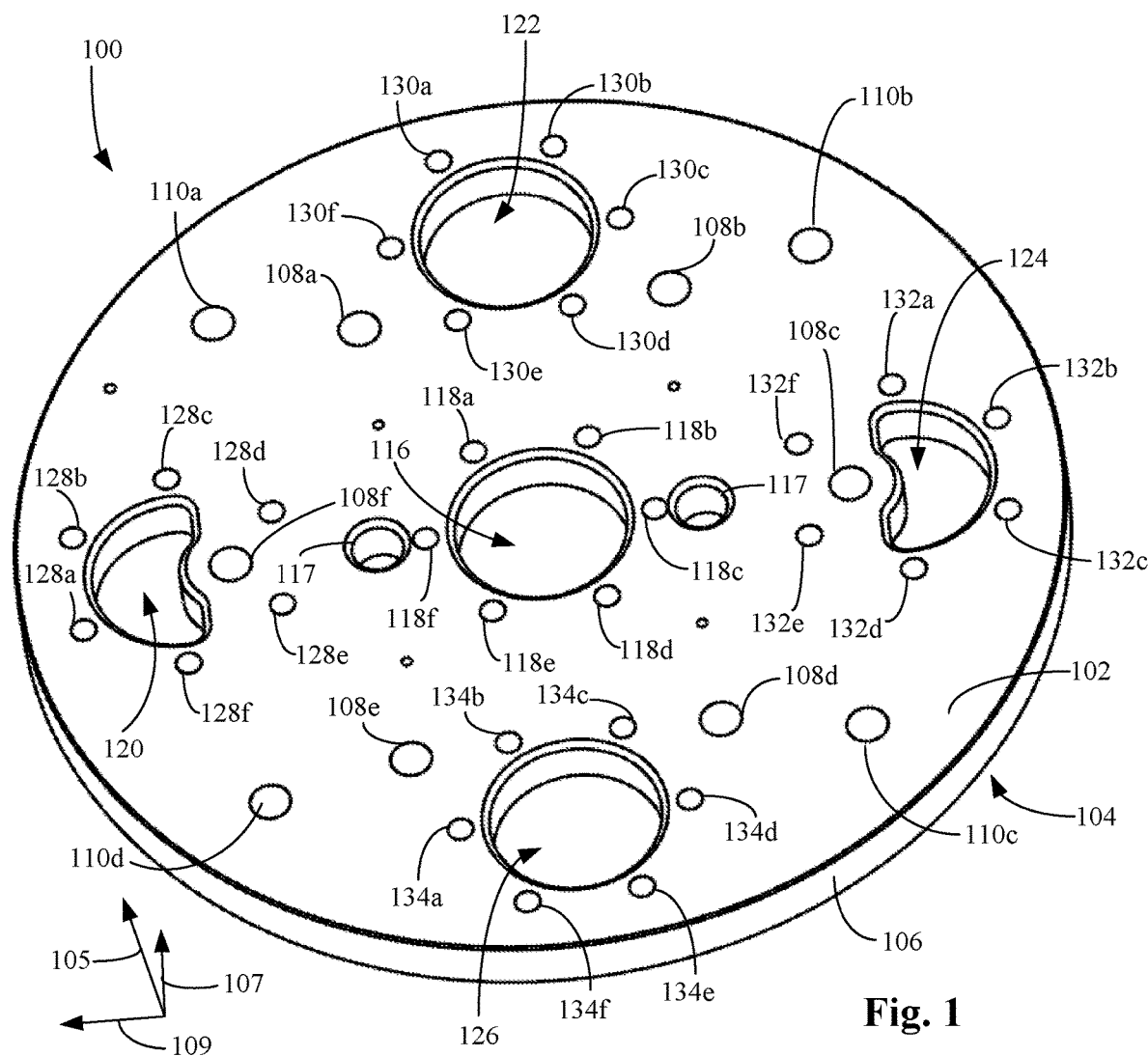
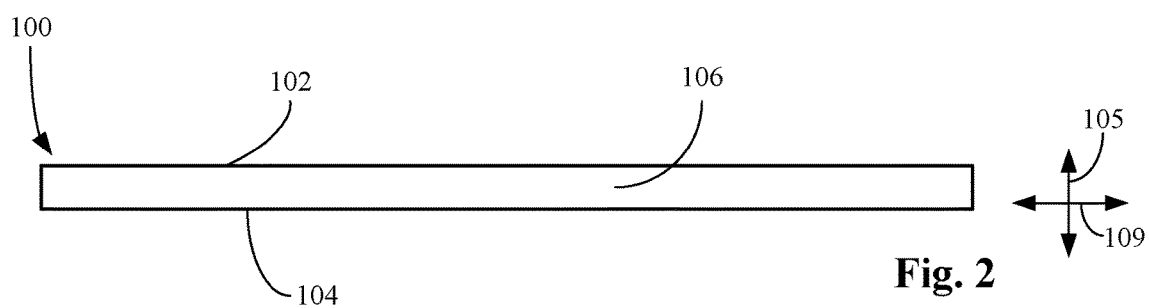

MOUNTING PLATE FOR MEDICAL DEVICE SUSPENSION SYSTEM

FIELD OF INVENTION

This application relates generally to a mounting plate for a medical device suspension system for use in, for example, a hospital examination room, a clinic, a surgery room or an emergency room; and more particularly to a mounting plate for a medical device suspension system having four mounting positions for auxiliary spindles.

BACKGROUND

Medical device suspension systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. For purposes of mounting a medical device suspension system, a structural plate is provided as part of the building structure (e.g., at the ceiling or wall). A mounting plate is utilized to mount the medical device suspension system to the structural plate.

The standardized mounting pattern of the structural plate varies depending on the geographic location. For example, the standardized mounting pattern for many countries (e.g., many European countries) is a hexagon pattern. This hexagon pattern has a bolt circle diameter of about 270 mm (10.63 inches), a hole to hole distance of about 135 mm (5.31 inches), and a bolt diameter of about 16 mm (⅝ inch). The hexagon mounting pattern is sometimes also used in the U.S., but another U.S. standardized pattern is a square (rectangular) mounting pattern. This square (rectangular pattern has a bolt circle diameter of about 368 mm (14.5 inches), a hole to hole distance of about 260 mm (10.25 inches), and a bolt diameter of about 16 mm (⅝ inch). Mounting plates are typically provided with both patterns for purposes of universal compatibility.

The medical device support system typically includes a central shaft or support column that is mounted to the mounting plate, and one or more generally horizontal extension arms mounted for rotational movement about the shaft. Some medical device support systems may also have one or two primary auxiliary spindle mounts radially located from the central axis spindle mount that allow additional auxiliary arm mounting options. However, the number of auxiliary spindle mounts on the mounting plate has been limited due much in part to the standardized hexagon mounting pattern, as well as space considerations that may limit the overall size of the mounting plate.

SUMMARY OF INVENTION

The application relates to a mounting plate for a medical device suspension system that may provide an increased number of mounting positions, despite the mounting plate including a hexagon mounting pattern. For example, the mounting plate may provide four mounting positions for auxiliary spindles. The mounting plate may provide improved versatility with respect to auxiliary arm mounting options. This allows, for example, for a greater number of auxiliary arms to be mounted to the device. Also, in embodiments where a lower number of auxiliary arms are used than available mounting positions, the mounting position of the auxiliary spindles can be changed without needing to reorient the mounting plate.

According to one aspect of the present disclosure, a mounting plate for a medical device support system includes: opposed major surfaces spaced apart from one another in a thickness direction; a group of plate mounting orifices arranged in a hexagon pattern, the plate mounting orifices of the group of plate mounting orifices extending through the opposed major surfaces in the thickness direction, the group of plate mounting orifices defining a perimeter of an area at the major surfaces; a primary orifice extending through the opposed major surfaces in the thickness direction, and a group of primary spindle mounting orifices surrounding the primary orifice and extending through the opposed major surfaces in the thickness direction, the primary orifice and the primary spindle mounting orifices located within the area defined by the group of plate mounting orifices; and an auxiliary orifice extending through the opposed major surfaces in the thickness direction and a group of auxiliary spindle mounting orifices surrounding the auxiliary orifice and extending through the opposed major surfaces in the thickness direction, the group of auxiliary spindle mounting orifices defining a perimeter of an auxiliary spindle mounting area at the major surfaces, one of the plate mounting orifices of the group of plate mounting orifices located within the auxiliary spindle mounting area defined by the group of auxiliary spindle mounting orifices.

In some embodiments, the mounting plate further includes an additional auxiliary orifice extending through the opposed major surfaces in the thickness direction and an additional group of auxiliary spindle mounting orifices surrounding the auxiliary orifice and extending through the opposed major surfaces in the thickness direction, the additional group of auxiliary spindle mounting orifices defining a perimeter of an additional auxiliary spindle mounting area at the major surfaces, the plate mounting orifices of the group of plate mounting orifices arranged outside the additional auxiliary spindle mounting area defined by the additional group of auxiliary spindle mounting orifices. In some embodiments, an area of the additional auxiliary orifice is at least 80% of the auxiliary spindle mounting area defined by the group of auxiliary spindle mounting orifices. In some embodiments, the auxiliary orifice and the additional auxiliary orifice are radially arranged about the primary orifice within a range of 80° to 100° from one another.

In some embodiments, the mounting plate includes three additional auxiliary orifices extending through the opposed major surfaces in the thickness direction, and respective additional groups of auxiliary spindle mounting orifices surrounding the auxiliary orifice and extending through the opposed major surfaces, each additional group of auxiliary spindle mounting orifices associated with a respective one of the additional auxiliary orifices, wherein: one of the additional groups of auxiliary spindle mounting orifices define a perimeter of a first auxiliary spindle mounting area at the major surfaces, another one of the plate mounting orifices of the group of plate mounting orifices located within the first auxiliary spindle mounting area defined by the one of the additional groups of auxiliary spindle mounting orifices; a second of the additional groups of auxiliary spindle mounting orifices define a perimeter of a second additional auxiliary spindle mounting area at the major surfaces, the plate mounting orifices of the group of plate mounting orifices arranged outside the additional auxiliary spindle mounting area defined by the second of the additional groups of auxiliary spindle mounting orifices; and a third of the additional groups of auxiliary spindle mounting orifices define a perimeter of a third additional auxiliary spindle mounting area at the major surfaces, the plate mounting orifices of the group of plate mounting orifices arranged outside the additional auxiliary spindle mounting area defined by the third of the additional groups of auxiliary spindle mounting orifices. In some embodiments, the auxiliary orifice and the additional auxiliary orifices are radially located around the primary orifice. In some embodiments, the auxiliary orifice and one of the additional auxiliary orifices are noncircular. In some embodiments, two of the additional auxiliary orifices are circular and are opposed one another in a first direction, the auxiliary orifice and one of the additional auxiliary orifices are noncircular auxiliary orifices are opposed one another in a second direction arranged 80° to 100° relative to the first direction.

In some embodiments, the auxiliary orifice is a noncircular orifice.

In some embodiments, the auxiliary orifice includes a semi-annular perimeter.

In some embodiments, an area of the auxiliary orifice is at least 40% of the area defined by the group of auxiliary spindle mounting orifices.

In some embodiments, the mounting plate further includes an additional group of plate mounting orifices arranged in a rectangular pattern, the plate mounting orifices of the additional group of plate mounting orifices extending through the opposed major surfaces in the thickness direction, the additional group of plate mounting orifices defining a perimeter of an area at the major surfaces.

In accordance with another aspect of the present disclosure, a medical device suspension system includes: the mounting plate of one or more of the above-described embodiments; a primary spindle mounted to mounting plate via the primary spindle mounting orifices such that an interior volume of the primary spindle is in fluid communication with the primary orifice; and an auxiliary spindle mounted to the mounting plate via the auxiliary spindle mounting orifices associated with one of the respective auxiliary orifices such that an interior volume of the auxiliary spindle is in fluid communication with the one of the respective auxiliary orifices.

In some embodiments, the mounting plate further includes an additional auxiliary orifice extending through the opposed major surfaces in the thickness direction and an additional group of auxiliary spindle mounting orifices surrounding the auxiliary orifice and extending through the opposed major surfaces in the thickness direction, the additional group of auxiliary spindle mounting orifices defining a perimeter of an additional auxiliary spindle mounting area at the major surfaces, the plate mounting orifices of the group of plate mounting orifices arranged outside the additional auxiliary spindle mounting area defined by the additional group of auxiliary spindle mounting orifices; and the medical device suspension system further includes an additional auxiliary spindle mounted to the mounting plate via the additional auxiliary spindle mounting orifices associated with the additional auxiliary orifice such that an interior volume of the additional auxiliary spindle is in fluid communication with the additional auxiliary orifice.

In accordance with another aspect of the present disclosure, a mounting plate for a medical device support system includes: opposed major surfaces spaced apart from one another in a thickness direction; a group of plate mounting orifices arranged in a hexagon pattern, the plate mounting orifices of the group of plate mounting orifices extending through the opposed major surfaces in the thickness direction, the group of plate mounting orifices defining a perimeter of an area at the major surfaces; and a group of auxiliary spindle mounting orifices extending through the opposed major surfaces in the thickness direction and defining a perimeter of an auxiliary spindle mounting area at the major surfaces, one of the plate mounting orifices of the group of plate mounting orifices located within the auxiliary spindle mounting area defined by the group of auxiliary spindle mounting orifices.

In some embodiments, the mounting plate further includes an auxiliary orifice extending through the opposed major surfaces in the thickness direction and located within the auxiliary spindle mounting area defined by the group of auxiliary spindle mounting orifices.

In some embodiments, the auxiliary orifice is a noncircular orifice.

In some embodiments, the auxiliary orifice includes a semi-annular perimeter.

In some embodiments, an area of the auxiliary orifice is at least 40% and less than 75% of the area defined by the group of auxiliary spindle mounting orifices.

In some embodiments, the mounting plate includes three additional groups of auxiliary spindle mounting orifices extending through the opposed major surfaces, wherein: one of the additional groups of auxiliary spindle mounting orifices define a perimeter of a first auxiliary spindle mounting area at the major surfaces, another one of the plate mounting orifices of the group of plate mounting orifices located within the first auxiliary spindle mounting area defined by the one of the additional groups of auxiliary spindle mounting orifices; a second of the additional groups of auxiliary spindle mounting orifices define a perimeter of a second additional auxiliary spindle mounting area at the major surfaces, the plate mounting orifices of the group of plate mounting orifices arranged outside the additional auxiliary spindle mounting area defined by the second of the additional groups of auxiliary spindle mounting orifices; and a third of the additional groups of auxiliary spindle mounting orifices define a perimeter of a third additional auxiliary spindle mounting area at the major surfaces, the plate mounting orifices of the group of plate mounting orifices arranged outside the additional auxiliary spindle mounting area defined by the third of the additional groups of auxiliary spindle mounting orifices.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the present disclosure.

FIG. 1 is a schematic perspective view of a mounting plate in accordance with an embodiment of the present disclosure.

FIG. 2 is a schematic side view of the mounting plate of FIG. 1.

DETAILED DESCRIPTION

Figure 3:
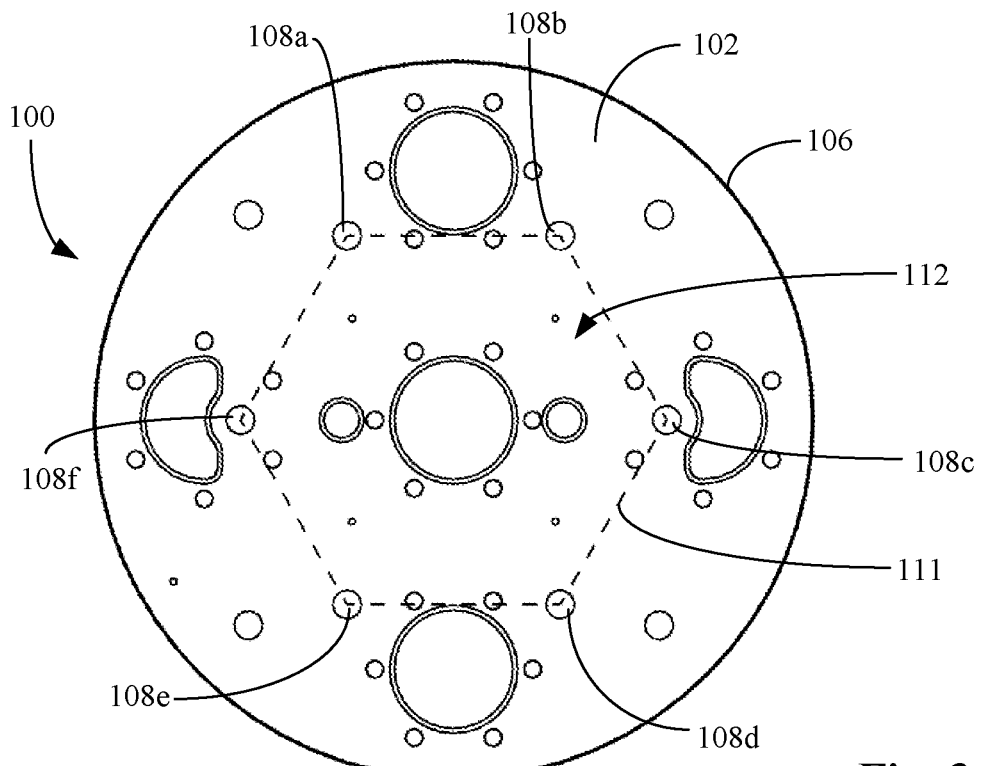
FIGS. 3-6 are schematic top views of the mounting plate of FIG. 1.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

With initial reference to FIGS. 1 and 2, an exemplary mounting plate is shown at 100. The mounting plate is a solid article of manufacture made from, for example, a metal, metal alloy, plastic, polymer, or other appropriate material. The mounting plate 100 includes a first major surface 102 and a second major surface 104 opposite the first major surface 102. The length and width dimensions of each of the major surfaces 102, 104 are greater, typically ten or more times greater, than the thickness of the mounting plate 100. In some embodiments, the diameter of the mounting plate 100 may be about 425 mm to about 500 mm. In other embodiments, the diameter of the mounting plate 100 may be about 450 mm to about 460 mm. The thickness is the dimension of the mounting plate 100 in a thickness direction 105 orthogonal to the major surfaces 102, 104. The thickness of the mounting plate 100 may be, for example, about 1 millimeter (mm) to about 50 mm. In other embodiments, the thickness of the mounting plate 100 may be about 20 mm to about 30 mm. In other embodiments, the thickness of the mounting plate 100 may be about 25 mm. In the illustrated embodiment, the major surfaces 102, 104 are planar. In other embodiments, at least a portion of the major surfaces 102, 104 of the mounting plate 100 may be curved in one or more directions (e.g., about an axis extending along direction 107 and/or extending along direction 109).

At least one side surface extends between the major surfaces 102, 104 of the mounting plate 100 in the thickness direction 105. The total number of side surfaces depends on the configuration of the mounting plate. In the case where the mounting plate 100 is circular (e.g., as shown in FIG. 1), the mounting plate 100 has one side surface 106. Other mounting plate shapes result in a corresponding number of side surfaces. Depending on the shape of the mounting plate 100, each side surface may be straight or curved, and adjacent side surfaces may meet at a vertex or join in a curve. Moreover, each side surface may include one or more straight portions connected to one or more curved portions. As described below, the mounting plate 100 may additionally include one or more side surfaces defined by the perimeter of an orifice extending through the light guide in the thickness direction. Each side surface defined by the perimeter of an orifice extending through the mounting plate 100 will hereinafter be referred to as an internal side surface.

The mounting plate 100 includes plate mounting orifices arranged in one or more patterns for mounting to a structural plate of a building. In the embodiment shown, one group of plate mounting orifices 108a, 108b, 108c, 108d, 108e, and 108f is arranged in a hexagon pattern and spaced apart from one another in such a manner that the mounting plate may mount to a structural plate having a hexagon mounting pattern. The plate mounting orifices 108a, 108b, 108c, 108d, 108e, and 108f extend through the opposed major surfaces 102, 104 in the thickness direction 105. Such a hexagon pattern is typically used as a standardized mounting pattern for medical device suspension systems in health treatment settings such as hospital examination rooms, clinics, surgery rooms and emergency rooms. As such, in some embodiments, the hexagon mounting pattern has one or more of a bolt circle diameter of about 270 mm (10.63 inches), a hole to hole distance of about 135 mm (5.31 inches), and a bolt diameter of about 16 mm (⅝ inch). In some embodiments, the respective internal side surfaces of the plate mounting orifices 108a, 108b, 108c, 108d, 108e, and 108f are smooth surfaces that allow for mounting hardware (e.g., screws, rods, bars, etc.) to pass therethrough and be secured, for example, via threaded nuts positioned at the major surfaces of the mounting plate. In other embodiments, the plate mounting orifices 108a, 108b, 108c, 108d, 108e, and 108f include threads (not shown) at their respective internal side surfaces that may allow for mounting of the mounting plate to the structural plate (e.g., via screws, threaded bars or rods, etc.).

As an alternative to structural plates having a hexagon mounting pattern, some structural plates (e.g., some in the U.S.) have a square (rectangular) mounting pattern. Accordingly, in some embodiments such as that shown in the figures, the mounting plate also includes another group of plate mounting orifices 110a, 110b, 110c, 110d arranged in a square (rectangular) pattern. In some embodiments, the square (rectangular) mounting pattern is the standardized mounting pattern having one or more of a bolt circle diameter of 368 mm (14.5 inches), a hole to hole distance of 260 mm (10.25 inches), and a bolt diameter of 16 mm (⅝ inch). The plate mounting orifices 110a, 110b, 110c, 110d extend through the opposed major surfaces 102, 104 in the thickness direction 105. In some embodiments, the respective internal side surfaces of the plate mounting orifices 110a, 110b, 110c, 110d are smooth surfaces that allow for mounting hardware (e.g., screws, rods, bars, etc.) to pass therethrough and be secured, for example, via threaded nuts positioned at the major surfaces of the mounting plate. In other embodiments, the plate mounting orifices 110a, 110b, 110c, 110d include threads (not shown) at their respective internal side surfaces that may allow for mounting of the mounting plate to the structural plate (e.g., via screws, threaded bars or rods, etc.). However, it will be understood that in some embodiments, the mounting plate 100 may only include the group of plate mounting orifices arranged in the hexagon pattern.

Figure 4:
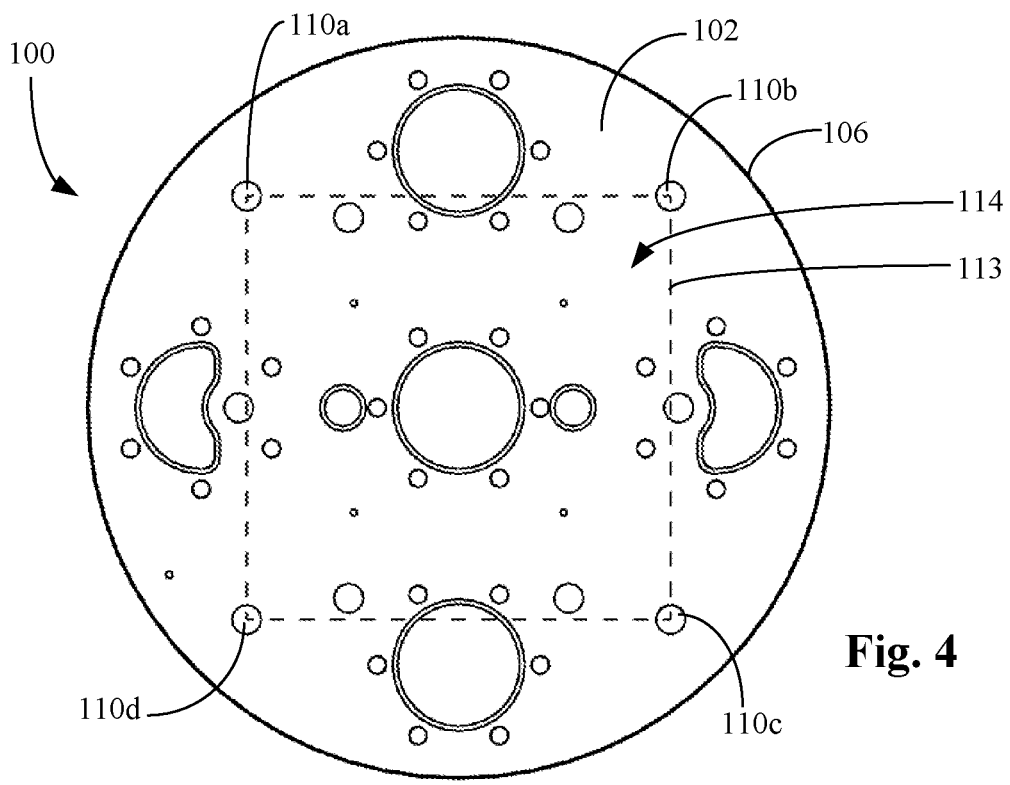

With exemplary reference to FIG. 3, the hexagon pattern of plate mounting orifices 108a, 108b, 108c, 108d, 108e, and 108f define a perimeter 111 of an area 112 at the major surfaces of the mounting plate. As further shown in FIG. 4, the square pattern of plate mounting orifices 110a, 110b, 110c, 110d defines a perimeter 113 of an area 114 at the major surfaces of the mounting plate. In embodiments where the mounting plate includes both the hexagon pattern of plate mounting orifices 108a, 108b, 108c, 108d, 108e, and 108f and the square (rectangular) pattern of plate mounting orifices 110a, 110b, 110c, 110d, area 112 may at least partially overlap the area 114.

The mounting plate 100 includes a primary orifice 116 extending through the opposed major surfaces 102, 104 in the thickness direction 105. Primary spindle mounting orifices 118a, 118b, 118c, 118d, 118e, 118f surround the primary orifice and extend through the opposed major surfaces 102, 104 in the thickness direction 105. In some embodiments, the diameter of the primary orifice may be about 70 mm to about 80 mm. In other embodiments, the diameter of the primary orifice may be about 75 mm. In some embodiments, the diameter of each of the primary spindle mounting orifices 118a, 118b, 118c, 118d, 118e, 118f may be about 10 mm to about 12 mm. In some embodiments, the bolt circle diameter formed by the pattern of primary spindle mounting orifices 118a, 118b, 118c, 118d, 118e, 118f may be about 90 mm to about 110 mm. In other embodiments, the bolt circle diameter formed by the pattern of primary spindle mounting orifices 118a, 118b, 118c, 118d, 118e, 118f may be about 100 mm.

In some embodiments, the respective internal side surfaces of the primary spindle mounting orifices 118a, 118b, 118c, 118d, 118e, 118f are smooth surfaces that allow for mounting hardware (e.g., screws) to pass therethrough, for example, for securing a spindle to the mounting plate. In other embodiments, the primary spindle mounting orifices 118a, 118b, 118c, 118d, 118e, 118f include threads (not shown) at their respective internal side surfaces such that mounting hardware (e.g., a screw) may engage both the internal side surface of the mounting plate and the spindle for purposes of mounting a spindle to the mounting plate. In the embodiment shown, the primary spindle mounting orifices include six mounting orifices 118a, 118b, 118c, 118d, 118e, 118f configured in a hexagon pattern. In other embodiments, the primary spindle mounting orifices may include more than six mounting orifices (e.g., seven, eight, etc.) and be configured in a different pattern (e.g., heptagon, octagon, etc.); or may include less than six mounting orifices (e.g., five, four, three, two) and may be configured in a different pattern (e.g., pentagon, rectangle, triangle, etc.). The number and configuration of primary spindle mounting orifices may be any suitable number and configuration that allows a spindle to mount thereto.

In the embodiment shown, the primary orifice 116 and the primary spindle mounting orifices 118a, 118b, 118c, 118d, 118e, 118f are located within the area 112 defined by the hexagon pattern of orifices (and within the area 114 defined by the square (rectangular) pattern of orifices). As such, the primary orifice 116 and the primary spindle mounting orifices 118a, 118b, 118c, 118d, 118e, 118f may be located at a relatively central area of the major surfaces of the mounting plate 100, and may allow, for example, for a spindle to be mounted to the relatively central area of the major surface of the mounting plate 100. As described below, the primary orifice 116 may allow for one or more cables, wires, and the like to pass through the mounting plate into the internal volume of a spindle mounted to the primary spindle mounting orifices. In the embodiment shown, the primary orifice is a circular orifice. The circular orifice may allow for maximum area through which the cables, wires, etc. may pass. In other embodiments, the primary orifice may be another suitable shape. As further shown in the exemplary embodiment, in some embodiments, the primary orifice 116 and the primary spindle mounting orifices may also be located adjacent (or between) one or more cable orifices 117 extending through the opposed major surfaces 102, 104 of the mounting plate 100. In some embodiments, the diameter of each of the cable orifices 117 may be about 20 mm to about 26 mm. In other embodiments, the diameter of each of the cable orifices 117 may be about 22.5 mm.

The mounting plate 100 includes auxiliary orifices extending through the opposed major surfaces 102, 104 in the thickness direction. In the embodiment shown, the mounting plate 100 includes four auxiliary orifices 120, 122, 124, 126. In the embodiment shown, the auxiliary orifices 120, 122, 124, 126 are arranged radially around the primary orifice 116. Two auxiliary orifices 122, 126 are opposed one another in a first direction 107, and the other two auxiliary orifices 120, 124 are opposed one another in a second direction 109. In some embodiments, the second direction 109 is orthogonal the first direction 107 such that one of the auxiliary orifice and adjacent one of the additional auxiliary orifices are radially arranged about the primary orifice at 90° from one another. In some embodiments, the second direction 109 and the first direction 107 are with a range of 80° to 100° from one another such that one of the auxiliary orifice and adjacent one of the additional auxiliary orifices are radially arranged about the primary orifice within a range of 80° to 100° from one another.

Auxiliary spindle mounting orifices extend through the opposed major surfaces 102, 104 of the mounting plate 100 in the thickness direction 105, groups of which are respectively associated with and respectively surround the auxiliary orifices 120, 122, 124, 126. In the exemplary embodiment shown, auxiliary spindle mounting orifices 128a, 128b, 128c, 128d, 128e, 128f surround the auxiliary orifice 120; auxiliary spindle mounting orifices 130a, 130b, 130c, 130d, 130e, 130f surround the auxiliary orifice 122; auxiliary spindle mounting orifices 132a, 132b, 132c, 132d, 132e, 132f surround the auxiliary orifice 124; and auxiliary spindle mounting orifices 134a, 134b, 134c, 134d, 134e, 134f surround the auxiliary orifice 126. In some embodiments, the diameter of each of the auxiliary orifices 122, 126 (and the maximum diameter of each of auxiliary orifices 120, 124 as measured from a non-indented portion of the auxiliary orifice) may be about 70 mm to about 80 mm. In other embodiments, the diameter of each of the auxiliary orifices 122, 126 (and the maximum diameter of each of auxiliary orifices 120, 124 as measured from a non-indented portion of the auxiliary orifice) may be about 75 mm. In some embodiments, the diameter of each of the auxiliary spindle mounting orifices may be about 10 mm to about 12 mm. In some embodiments, the bolt circle diameter formed by the pattern of auxiliary spindle mounting orifices may be about 90 mm to about 110 mm. In other embodiments, the bolt circle diameter formed by the pattern of auxiliary spindle mounting orifices may be about 100 mm.

In some embodiments, the diameter of each of the auxiliary spindle mounting orifices may be about 10 mm to about 12 mm. In some embodiments, the bolt circle diameter formed by the pattern of auxiliary spindle mounting orifices may be about 90 mm to about 110 mm. In other embodiments, the bolt circle diameter formed by the pattern of auxiliary spindle mounting orifices may be about 100 mm.

In some embodiments, the respective internal side surfaces of the auxiliary spindle mounting orifices are smooth surfaces that allow for mounting hardware (e.g., screws) to pass therethrough, for example, for securing a spindle to the mounting plate. In other embodiments, the auxiliary spindle mounting orifices include threads (not shown) at their respective internal side surfaces such that mounting hardware (e.g., a screw) may engage both the internal side surface of the mounting plate and the spindle for purposes of mounting a spindle to the mounting plate. In the embodiment shown, for each auxiliary orifice, the auxiliary spindle mounting orifices associated therewith include six mounting orifices configured in a hexagon pattern. In other embodiments, the auxiliary spindle mounting orifices associated with a given auxiliary orifice may include more than six mounting orifices (e.g., seven, eight, etc.) and be configured in a different pattern (e.g., heptagon, octagon, etc.); or may include less than six mounting orifices (e.g., five, four, three, two) and may be configured in a different pattern (e.g., pentagon, rectangle, triangle, etc.). The number and configuration of auxiliary spindle mounting orifices associated with a given auxiliary orifice may be any suitable number and configuration that allows a spindle to mount thereto.

Figure 5:
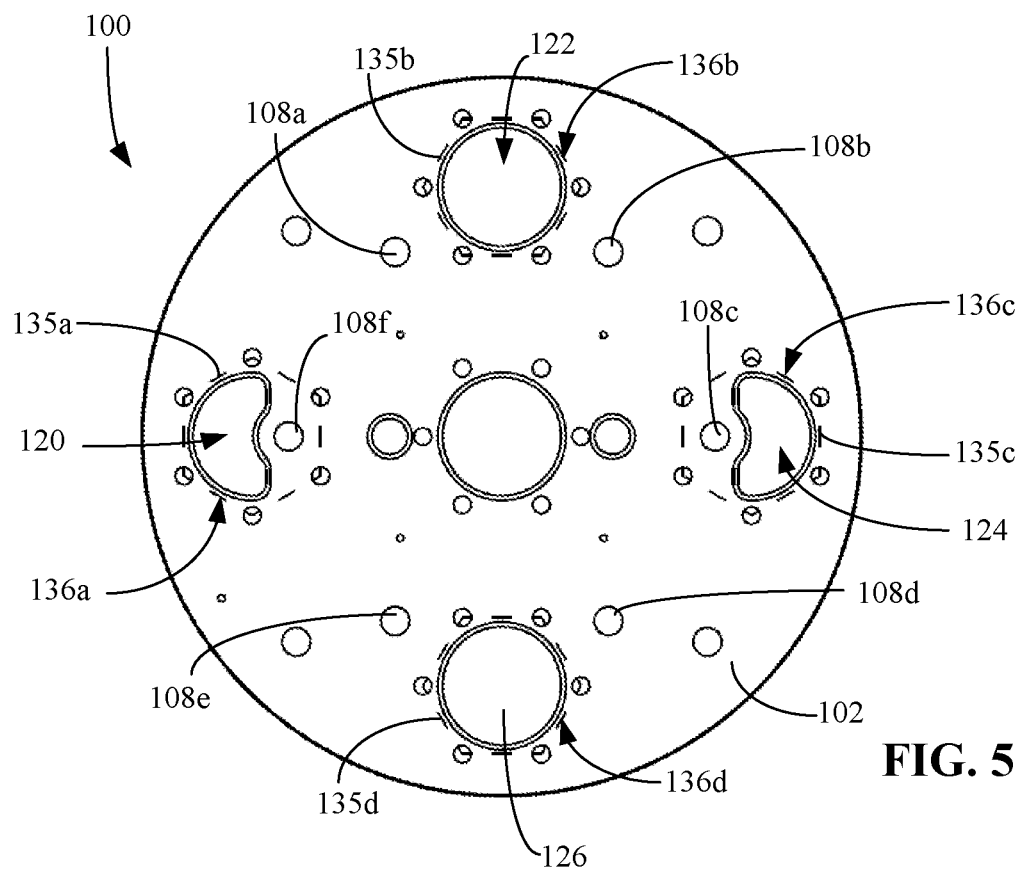
Figure 6:
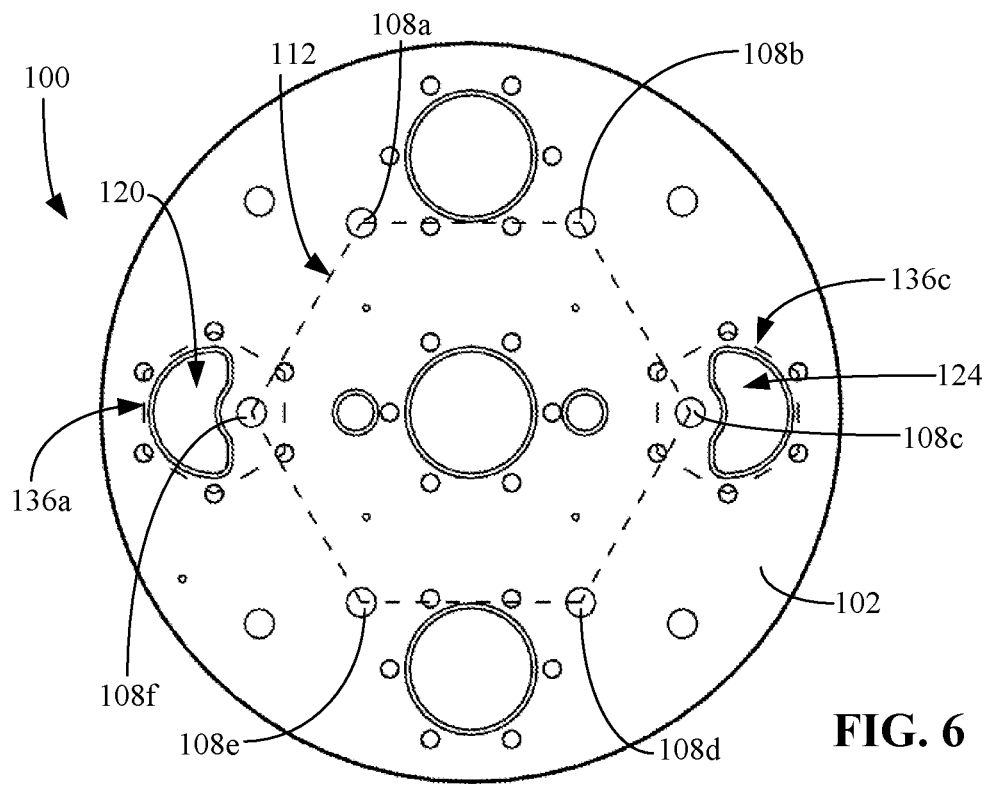

With reference to FIG. 5, each group of auxiliary spindle mounting orifices defines a perimeter 135a, 135b, 135c, 135d of a respective area at the major surfaces of the mounting plate. In the embodiment shown, each hexagon pattern of auxiliary spindle mounting orifices defines a respective area 136a, 136b, 136c, 136d. A respective auxiliary orifice is located in each of the areas.

In the embodiment shown, two of the auxiliary orifices and respective auxiliary spindle mounting orifices associated therewith are arranged with respect to the hexagon pattern of plate mounting orifices such that they are adjacent but not overlapping with the orifices of the hexagon mounting pattern. More specifically, with reference to FIGS. 1 and 5, the plate mounting orifices 108a, 108b are adjacent but are not within the area 136b defined by the auxiliary spindle mounting orifices 130a, 130b, 130c, 130d, 130e, 130f. Similarly, the spindle mounting orifices 108d and 108e are adjacent but are not within the area 136d defined by the auxiliary spindle mounting orifices 134a, 134b, 134c, 134d, 134e, 134f. As such, the auxiliary orifice located within the areas 136b and 136d may be configured to occupy the majority of the area defined by the auxiliary spindle mounting orifices. In some embodiments, the area of the auxiliary orifice is at least 70% of the area defined by the auxiliary spindle mounting orifices. In some embodiments the area of the auxiliary orifice is at least 80% of the area defined by the auxiliary spindle mounting orifices. In some embodiments the area of the auxiliary orifice is at least 90% of the area defined by the auxiliary spindle mounting orifices. As shown, the auxiliary orifices 122, 126 are circular orifices.

The other two of the auxiliary orifices and respective auxiliary spindle mounting orifices associated therewith are arranged with respect to the hexagon pattern of plate mounting orifices such each of the areas defined by the group of auxiliary spindle mounting orifices encompasses one of the plate mounting orifices of the hexagon plate mounting pattern. More specifically, with reference to FIGS. 1 and 5, the plate mounting orifice 108f is within the area 136a defined by the auxiliary spindle mounting orifices 128a, 128b, 128c, 128d, 128e, 128f. Similarly, the plate mounting orifice 108c is within the area 136c defined by the auxiliary spindle mounting orifices 132a, 132b, 132c, 132d, 132e, 132f. As shown in FIG. 5, for the group of auxiliary spindle mounting orifices surrounding auxiliary orifice 120 and the group of auxiliary spindle mounting orifices surrounding auxiliary orifice 124, a portion of the areas 136a and 136c at least partially overlap with area 112.

For each of the auxiliary orifices 120, 124, one of the hexagon pattern plate mounting orifices 108f, 108c is in a location that may not permit the auxiliary orifices 120, 124 to have the same size and shape as the auxiliary orifices 122, 128. More specifically, in the embodiment shown, both the auxiliary orifice 120 and the plate mounting orifice 108f are within the area 136a defined by the auxiliary spindle mounting orifices 128a, 128b, 128c, 128d, 128e, 128f. Similarly, both the auxiliary orifice 124 and the plate mounting orifice 108c are within the area 136c defined by the auxiliary spindle mounting orifices 132a, 132b, 132c, 132d, 132e, 132f.

The requisite size of the mounting plate may not permit the spacing and arrangement of four auxiliary orifices and auxiliary spindle mounting orifices to be provided in a manner that avoids an orifice of the hexagon pattern plate mounting orifices from interfering with at least one of the auxiliary orifices. For example, in some embodiments, the length and width dimensions of the mounting plate 100 orthogonal to the thickness direction are limited based on the surrounding structure provided in the environment in which the medical device suspension system is to be mounted. For example, with exemplary reference to FIGS. 7 and 8, in some embodiments the mounting plate when mounted to a structural plate at the ceiling of a room should be able to allow the components of the medical device suspension system to fit through a standard 2 foot by 2 foot opening in the ceiling (e.g., in place of a ceiling tile). Accordingly, in the embodiment shown in which the mounting plate 100 is circular, the diameter of the mounting plate is 2 feet or less. Because the hexagon shape mounting pattern is of a standard shape and size, this may impede at least some of the auxiliary orifices from being arranged in a manner where a plate mounting orifice from the hexagon pattern would not otherwise overlap with the auxiliary orifice.

In accordance with the present disclosure, the auxiliary orifices 120, 124 may be provided as non-circular orifices. As shown, in some embodiments, the auxiliary orifices 120, 124 are provided as semi-annular orifices. Although, in other embodiments, the auxiliary orifices 120, 124 may have a different shape that allows for accommodation of one or more cables to pass through the orifice. In some embodiments, the area of the auxiliary orifice 120, 124 is at least 40% (and in some embodiments also less than 75%) of the area defined by the auxiliary spindle mounting orifices. In some embodiments the area of the auxiliary orifice 120, 124 is at least 50% (and in some embodiments also less than 75%) of the area defined by the auxiliary spindle mounting orifices. In some embodiments the area of the auxiliary orifice 120, 124 is at least 60% (and in some embodiments also less than 75%) of the area defined by the auxiliary spindle mounting orifices. Configuration of the auxiliary orifices 120, 124 as the non-circular orifices may alleviate interference of the hexagon mounting pattern orifice with the auxiliary orifice, while also providing sufficient area to allow for one or more cables, wires, and the like to pass through the mounting plate into the internal volume of a spindle mounted to the primary spindle mounting orifices.

Figure 7:
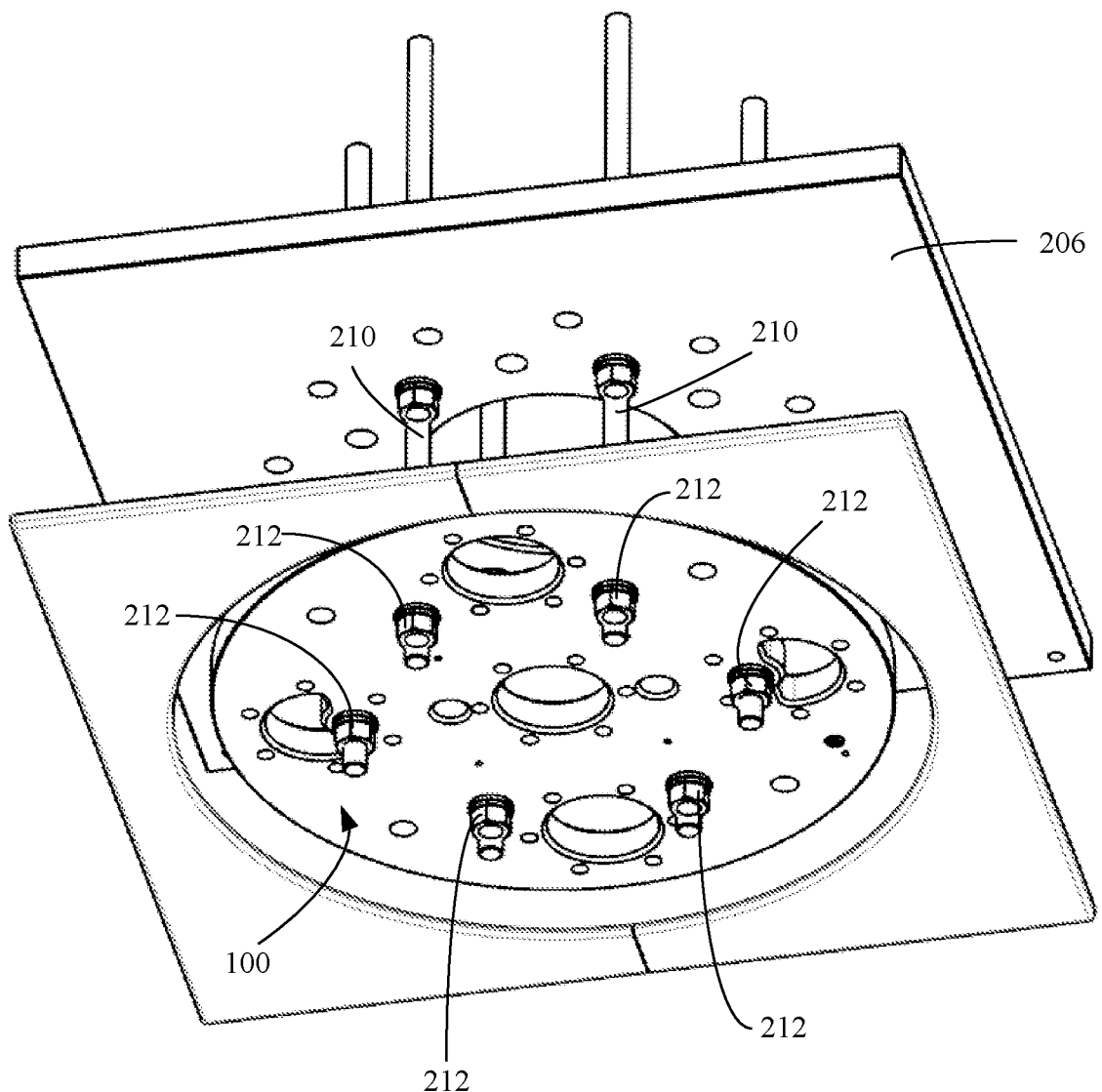
FIG. 7 is a schematic perspective view of the mounting plate of FIG. 1 mounted to an exemplary structural plate.
Figure 8:
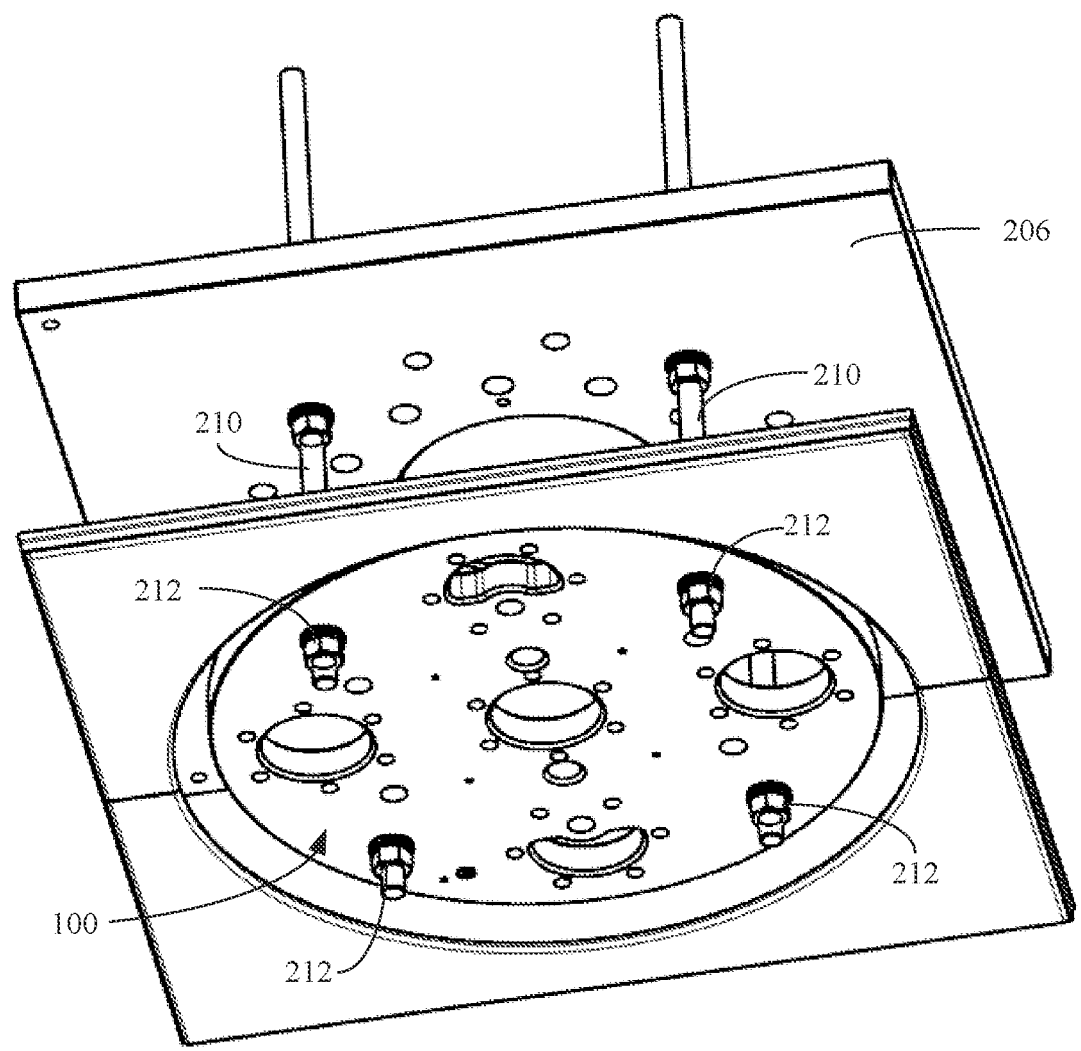
FIG. 8 is a schematic perspective view of the mounting plate of FIG. 1 mounted to an exemplary structural plate.

Turning now to FIGS. 7 and 8, embodiments of the mounting plate mounted to a structural plate are shown. In FIG. 7, the mounting plate 100 is mounted to a structural plate 206 using six rods 210 via the hexagon mounting pattern. Each rod 210 passes through the mounting plate at a respective plate mounting orifice 108a, 108b, 108c, 108d, 108e, 108f, and threaded nuts 212 are attached to the rod at respective major surfaces of the mounting plate to retain the mounting plate in position (see also FIG. 10). In FIG. 8, the mounting plate 100 is mounted to a structural plate 206 using four rods 210 via the square (rectangular) mounting pattern. Each rod 210 passes through the mounting plate at a respective plate mounting orifice 110a, 110b, 110c, 110d, and threaded nuts 212 are attached to the rod at respective major surfaces of the mounting plate to retain the mounting plate in position.

Turning now to FIGS. 9-15, a medical device suspension system 200 may be mounted to the mounting plate 100. The mounting plate 100 increases the versatility of the manner in which the medical device suspension system can be assembled and configured. With initial reference to FIGS. 9 and 10, an exemplary configuration is shown in which parts of a medical device suspension system 200, namely a primary spindle 202 and an auxiliary spindle 204, are attached to the mounting plate 100. With specific reference to FIG. 10, in some embodiments, respective fasteners 214 (e.g., screws) pass through the primary spindle mounting orifices and are secured to the primary spindle. The primary spindle is mounted to mounting plate via the primary spindle mounting orifices such that an interior volume 216 of the primary spindle is in fluid communication with the primary orifice 116. Respective fasteners 214 (e.g., screws) pass through the auxiliary spindle mounting orifices and are secured to the auxiliary spindle 204. The auxiliary spindle is mounted to the mounting plate via the auxiliary spindle mounting orifices associated with one of the respective auxiliary orifices such that an interior volume 218 of the auxiliary spindle 204 is in fluid communication with the one of the respective auxiliary orifices 124.

Figure 9:
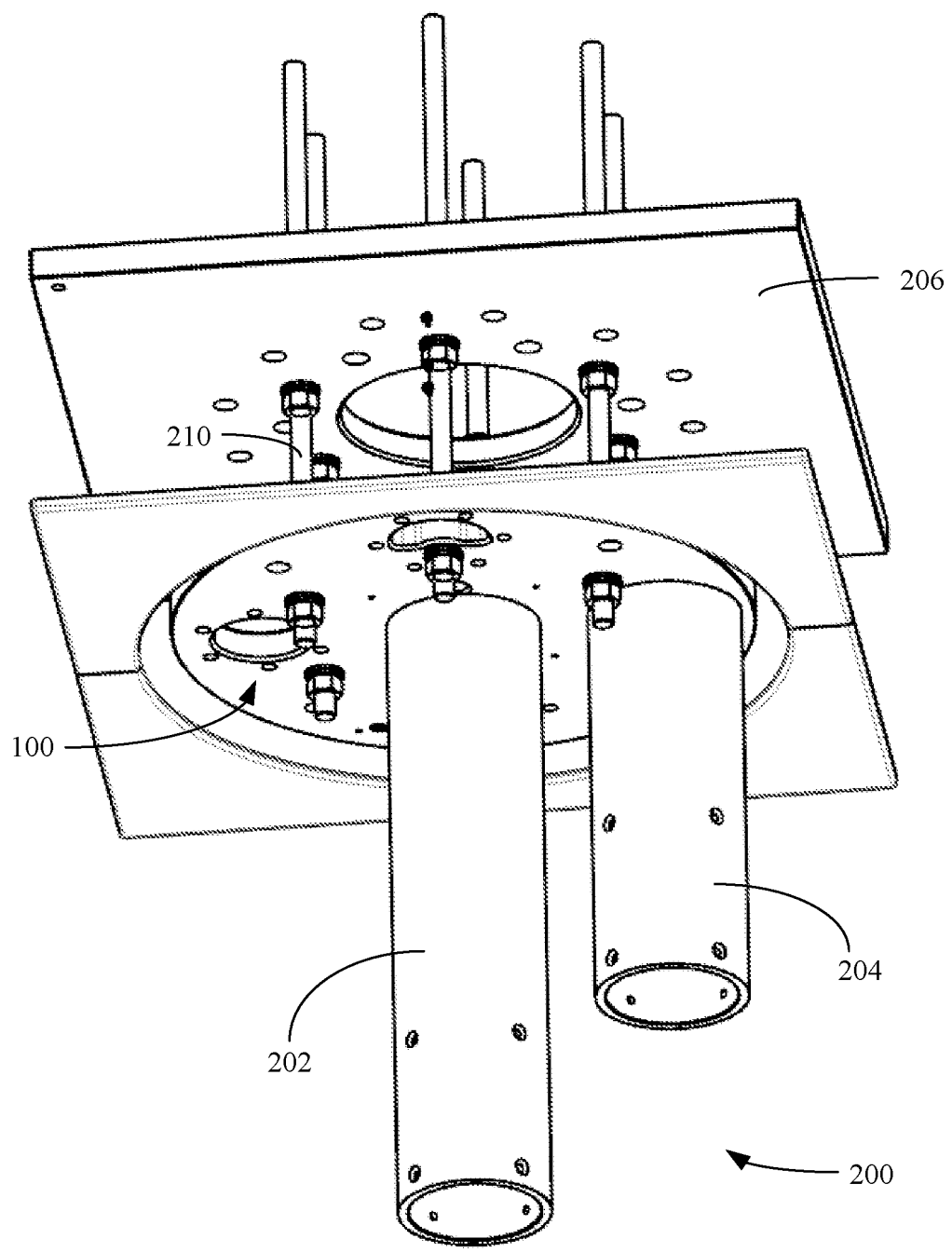
FIG. 9 is a schematic perspective view of the mounting plate of FIG. 1 mounted to an exemplary structural plate and parts of an exemplary medical device support system mounted to the mounting plate.
Figure 10:
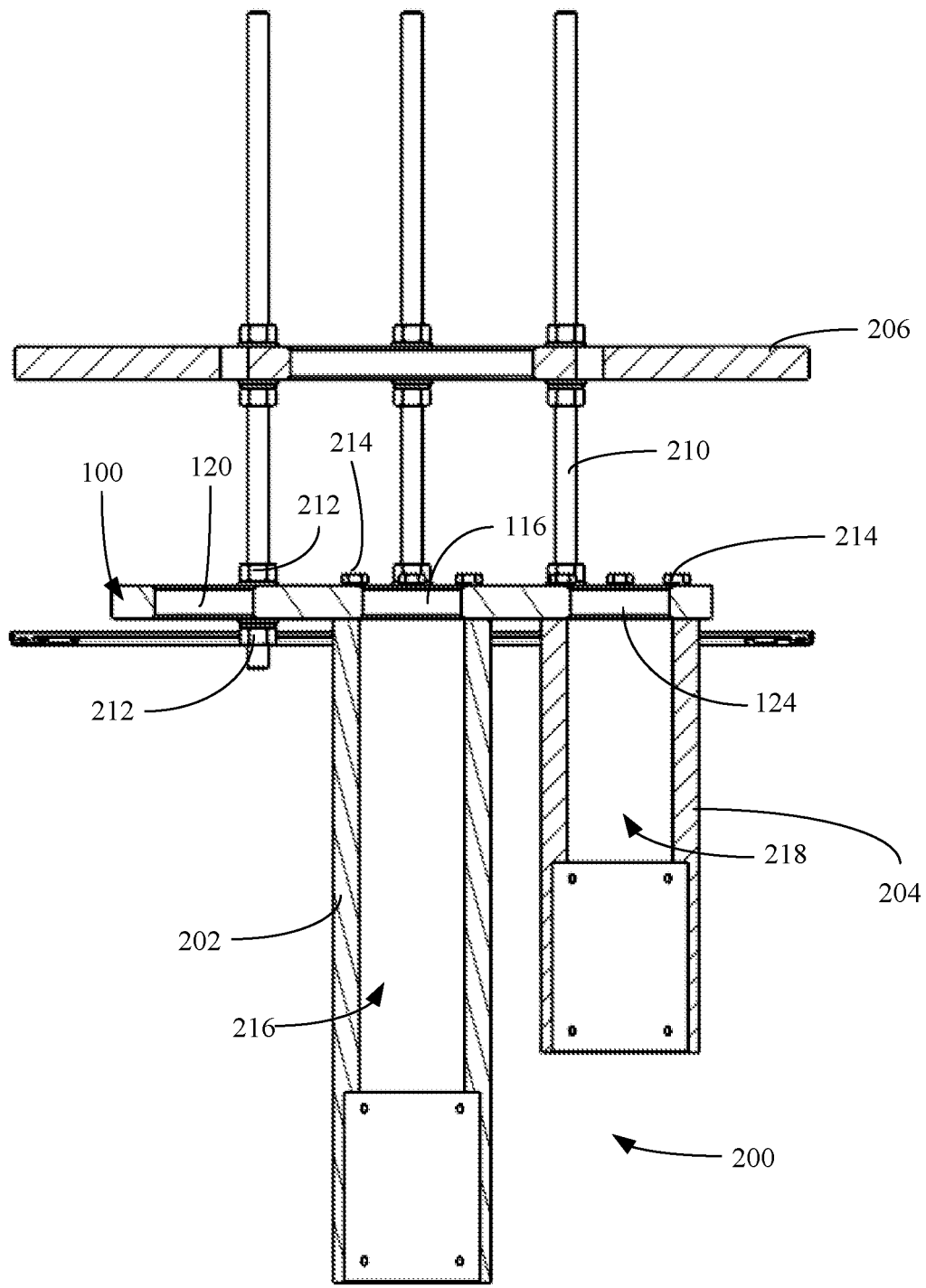
FIG. 10 is a schematic cross-sectional view of the mounting plate of FIG. 1 mounted to an exemplary structural plate and parts of an exemplary medical device support system mounted to the mounting plate.
Figure 11:
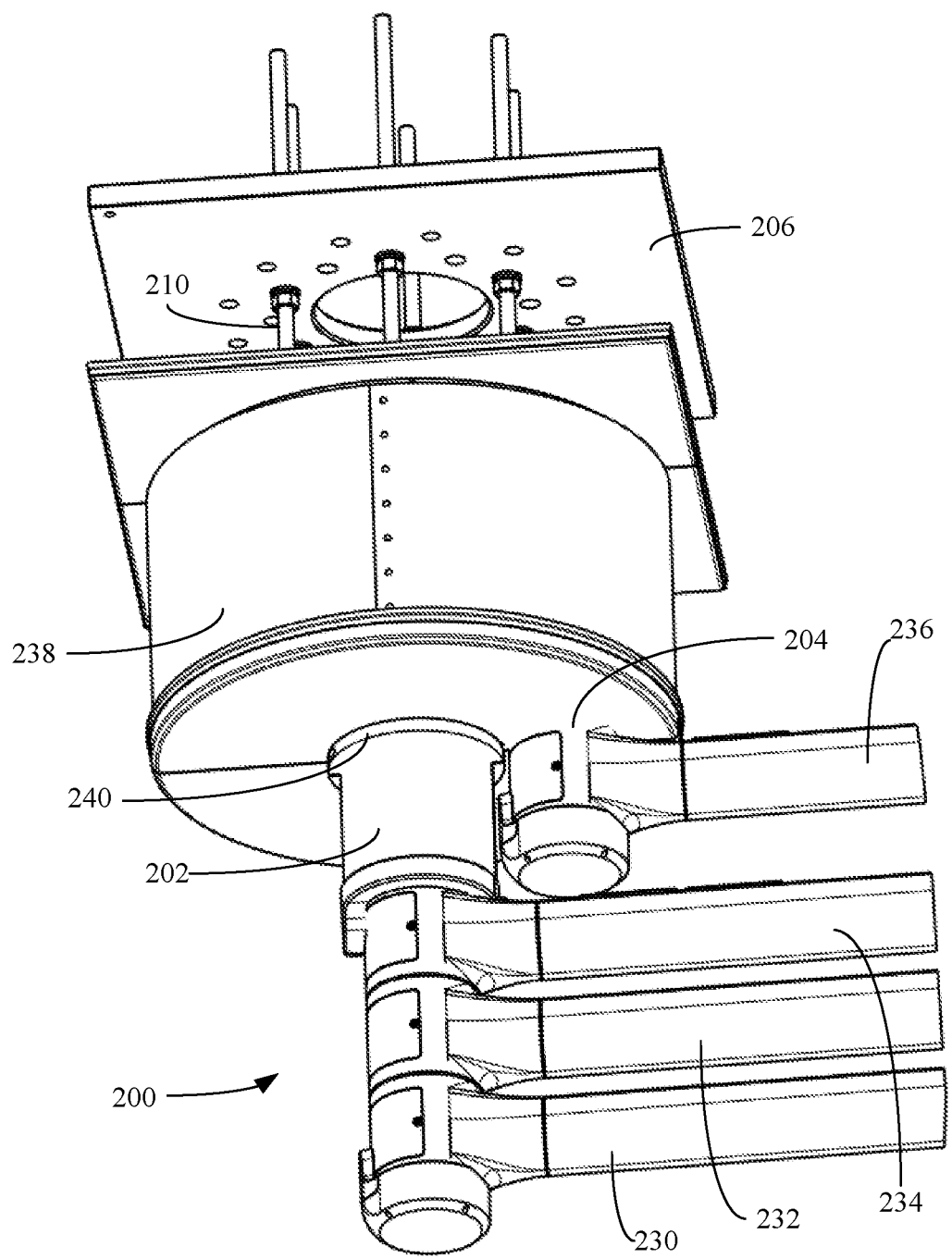
FIGS. 11-15 are a schematic perspective views of the mounting plate of FIG. 1 mounted to an exemplary structural plate and parts of exemplary medical device support systems mounted to the mounting plate.
Figure 12:
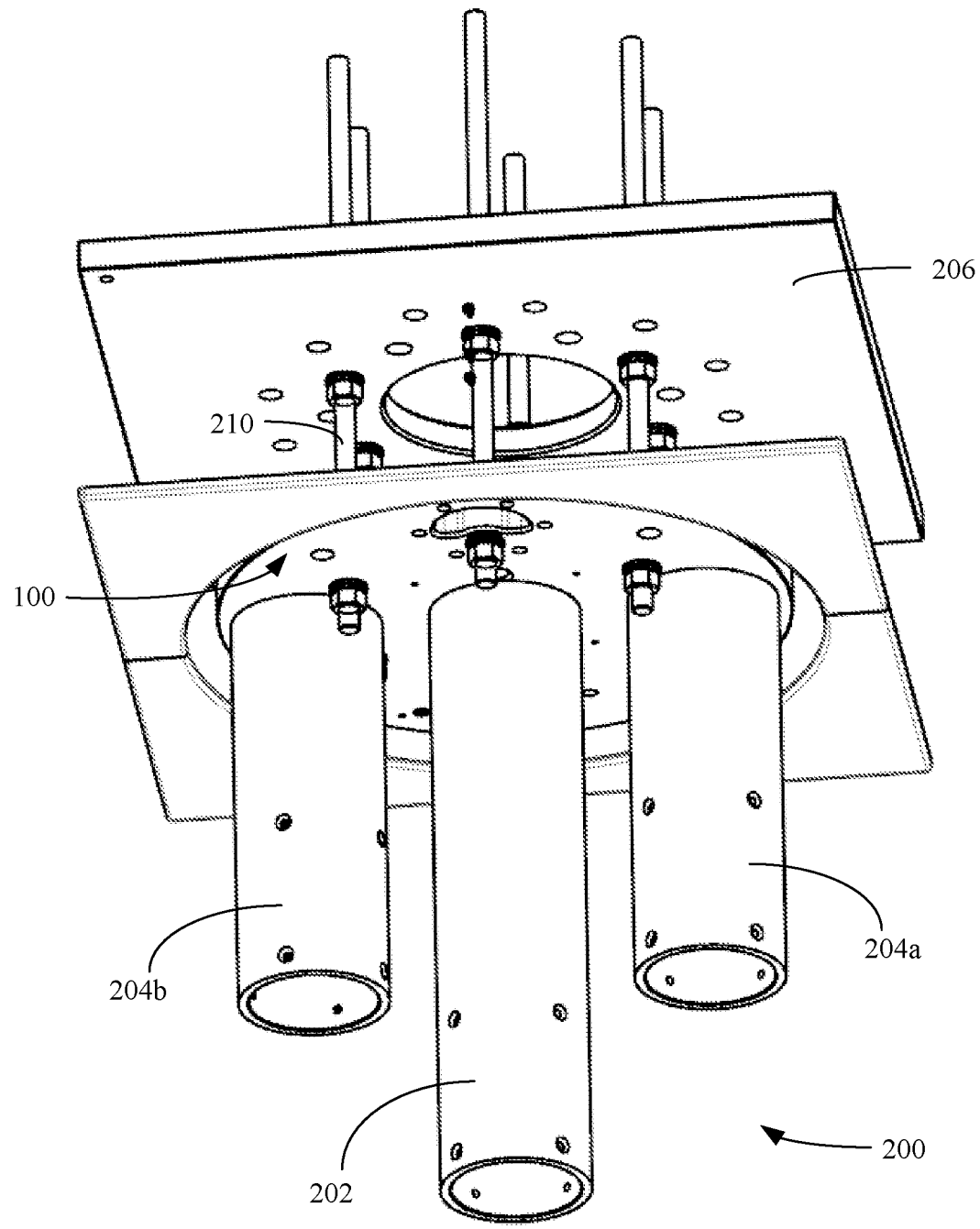
Figure 13:
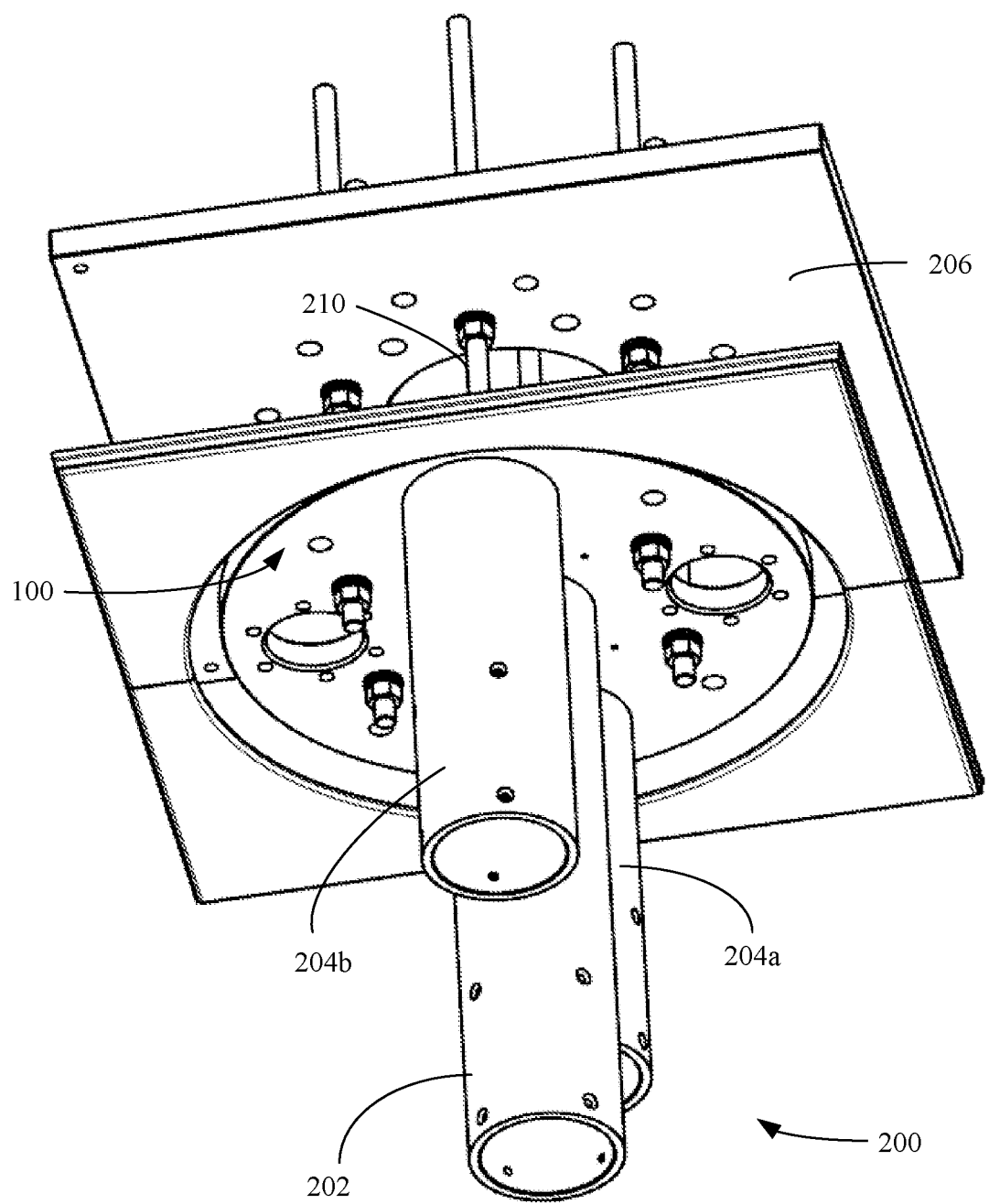
Figure 14:
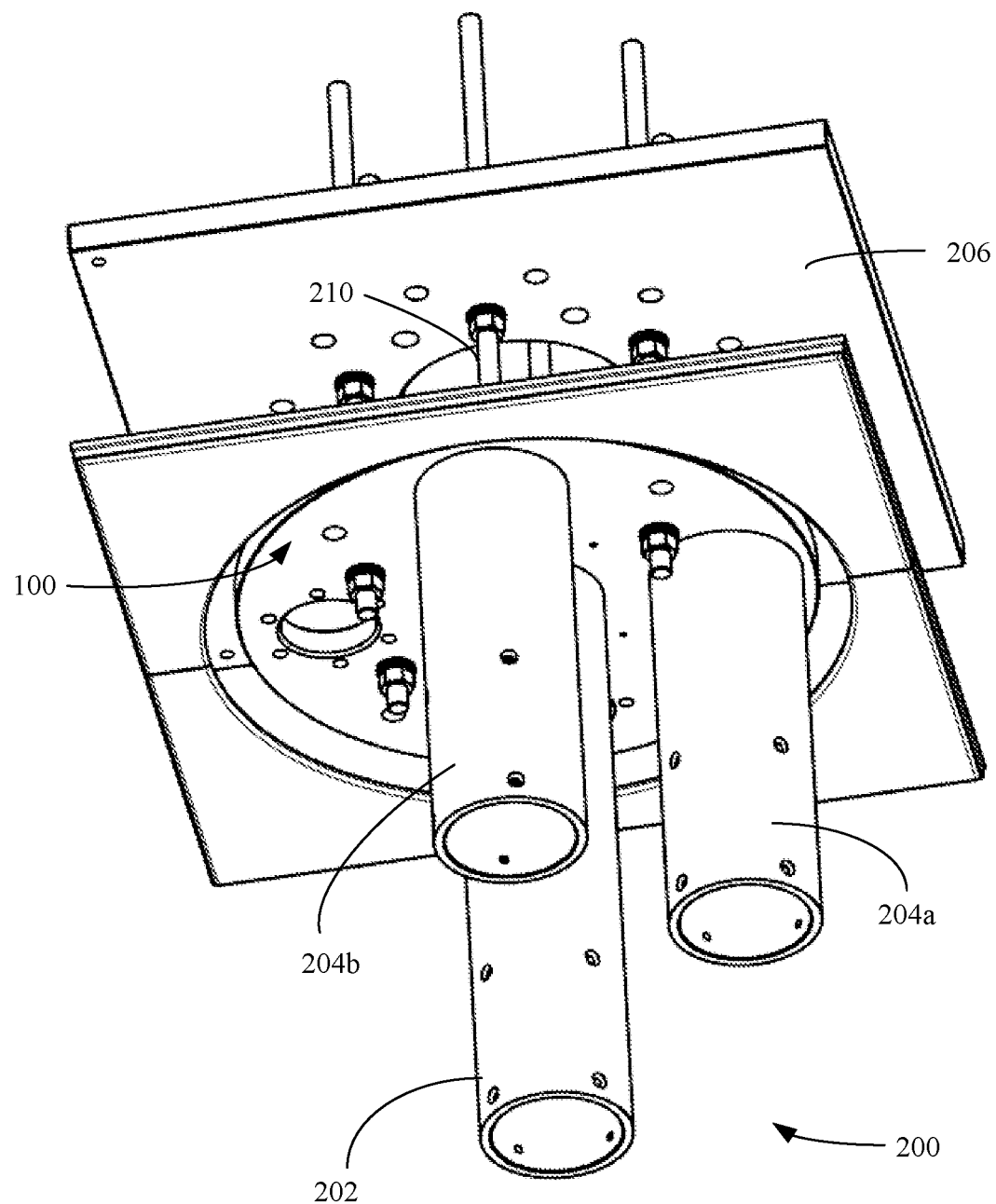
Figure 15:
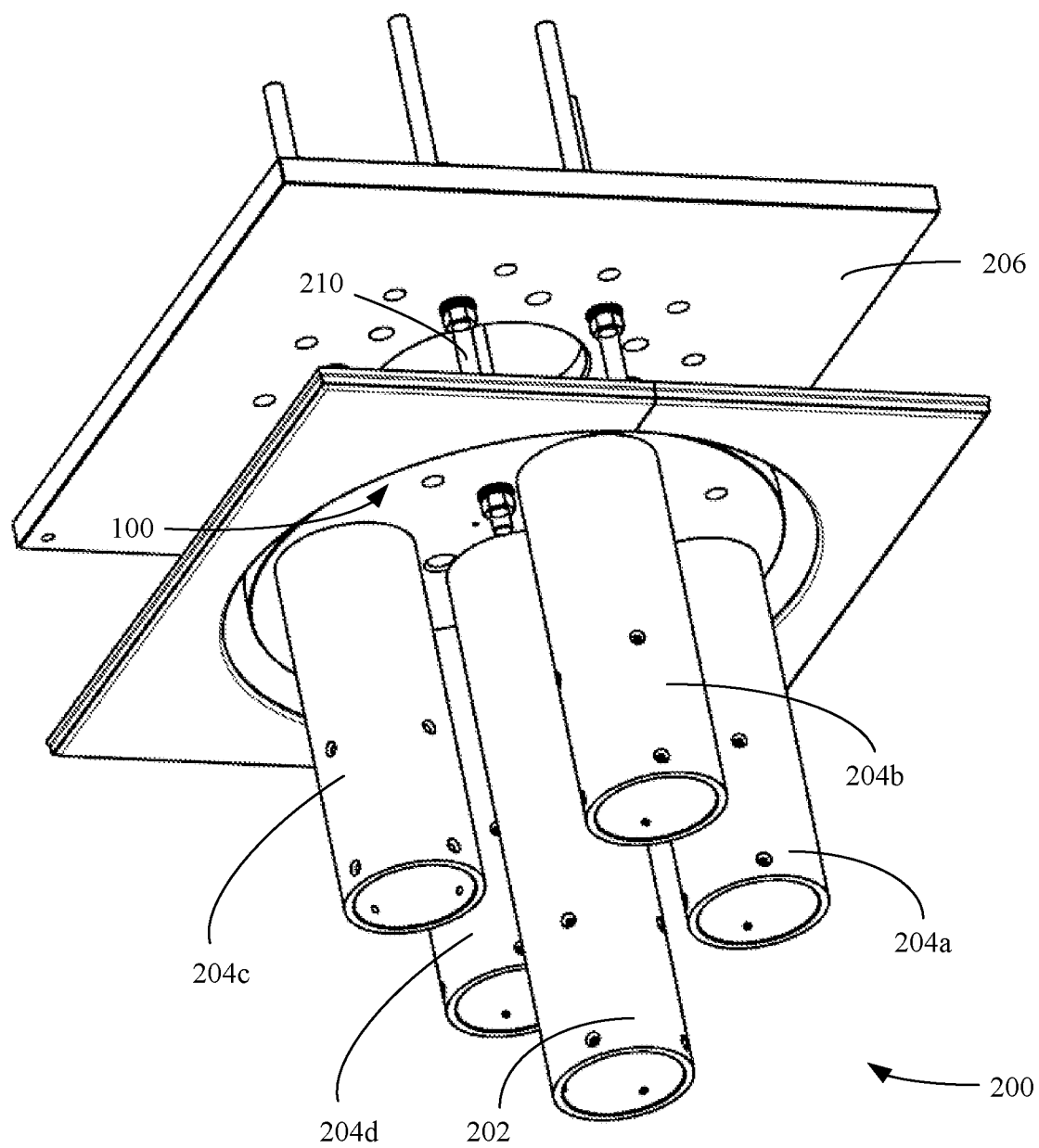

FIG. 11 shows an exemplary configuration similar to FIGS. 9 and 10, but including additional components of an medical device suspension system 200. More specifically, horizontal extension arms 230, 232, 234 are mounted to the primary spindle 202. An auxiliary arm 236 is also mounted to the auxiliary spindle 204. A cover 238 is also attached, which encloses the mounting plate and upper portion of the spindles 202, 204. The cover 238 may be retained, for example by a retaining ring 240 that is mounted to the primary spindle 202.

It will be appreciated that the auxiliary orifices allow for the auxiliary spindle to be mounted at any one of the auxiliary spindle locations. This may provide, for example, the flexibility to reconfigure the medical device suspension system without having to detach and adjust the positioning of the mounting plate.

The configuration of the auxiliary orifices and associated auxiliary spindle mounting orifices also may allow for more than one auxiliary spindle to be mounted to the mounting plate at one time; and these auxiliary spindles can be arranged in any one of several desired arrangements. For example, with additional reference to FIG. 12, an exemplary configuration of the medical device suspension system 200 includes two auxiliary spindles 204a, 204b mounted along a first direction 107 such that an interior volume of the auxiliary spindle 204a is in fluid communication with auxiliary orifice 122 and an interior volume of the auxiliary spindle 204b is in fluid communication with auxiliary orifice 126. With additional reference to FIG. 13, another exemplary configuration of the medical device suspension system 200 includes two auxiliary spindles 204a, 204b mounted along a second direction 109 such that an interior volume of the auxiliary spindle 204a is in fluid communication with auxiliary orifice 120 and an interior volume of the auxiliary spindle 204b is in fluid communication with auxiliary orifice 124. In this embodiment, the hexagon mounting pattern orifice 108f is in fluid communication with the interior volume of the auxiliary spindle 204a such that the mount passing through the hexagon mounting pattern orifice 108f is within the interior volume of the spindle 204a; and the hexagon mounting pattern orifice 108c is in fluid communication with the interior volume of the auxiliary spindle 204b such that the mount passing through the hexagon mounting pattern orifice 108c is within the interior volume of the spindle 204b. With additional reference to FIG. 14, another exemplary configuration of the medical device suspension system 200 includes two auxiliary spindles 204a, 204b mounted such that an interior volume of the auxiliary spindle 204a is in fluid communication with auxiliary orifice 122 and an interior volume of the auxiliary spindle 204b is in fluid communication with auxiliary orifice 124. In this embodiment, the hexagon mounting pattern orifice 108c is in fluid communication with the interior volume of the auxiliary spindle 204b such that the mount passing through the hexagon mounting pattern orifice 108c is within the interior volume of the spindle 204b. With additional reference to FIG. 15, another exemplary configuration of the medical device suspension system 200 includes four auxiliary spindles mounted to the mounting plate via the respective groups of auxiliary spindle mounting orifices. In still other embodiments (not shown), the medical device suspension system 200 may include three auxiliary spindles respectively mounted to the mounting plate 100 via three of the respective groups of auxiliary spindle mounting orifices.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A mounting plate for a medical device support system, comprising:

opposed major surfaces spaced apart from one another in a thickness direction;

a group of plate mounting orifices arranged in a regular hexagon pattern, the group of plate mounting orifices extending through the opposed major surfaces in the thickness direction and through the mounting plate to accommodate mounting hardware therethrough, the group of plate mounting orifices defining a perimeter of an area at the opposed major surfaces;

a primary orifice extending through the opposed major surfaces in the thickness direction, and a group of primary spindle mounting orifices surrounding the primary orifice and extending through the opposed major surfaces in the thickness direction, the primary orifice and the group of primary spindle mounting orifices located within the area defined by the group of plate mounting orifices; and an auxiliary orifice extending through the opposed major surfaces in the thickness direction and a group of auxiliary spindle mounting orifices surrounding the auxiliary orifice and extending through the opposed major surfaces in the thickness direction, the group of auxiliary spindle mounting orifices defining a perimeter of an auxiliary spindle mounting area at the opposed major surfaces, only one of the plate mounting orifices of the group of plate mounting orifices located within the auxiliary spindle mounting area defined by the group of auxiliary spindle mounting orifices.

2. The mounting plate of claim 1, further comprising an additional auxiliary orifice extending through the opposed major surfaces in the thickness direction and an additional group of auxiliary spindle mounting orifices surrounding the additional auxiliary orifice and extending through the opposed major surfaces in the thickness direction, the additional group of auxiliary spindle mounting orifices defining a perimeter of an additional auxiliary spindle mounting area at the opposed major surfaces, the plate mounting orifices of the group of plate mounting orifices arranged outside the additional auxiliary spindle mounting area defined by the additional group of auxiliary spindle mounting orifices.

3. The mounting plate of claim 2, wherein an area of the additional auxiliary orifice is at least 80% of the auxiliary spindle mounting area defined by the group of auxiliary spindle mounting orifices.

4. The mounting plate of claim 2, wherein the auxiliary orifice and the additional auxiliary orifice are radially arranged about the primary orifice within a range of 80° to 100° from one another.

5. The mounting plate of claim 1, wherein the mounting plate comprises three additional auxiliary orifices extending through the opposed major surfaces in the thickness direction, and respective additional groups of auxiliary spindle mounting orifices respectively surrounding the three additional auxiliary orifices and extending through the opposed major surfaces, each additional group of auxiliary spindle mounting orifices associated with a respective one of the additional auxiliary orifices, wherein:
   a first group of the additional groups of auxiliary spindle mounting orifices define a perimeter of a first additional auxiliary spindle mounting area at the opposed major surfaces, another one of the plate mounting orifices of the group of plate mounting orifices located within the first additional auxiliary spindle mounting area defined by the first group of the additional groups of auxiliary spindle mounting orifices;
   a second group of the additional groups of auxiliary spindle mounting orifices define a perimeter of a second additional auxiliary spindle mounting area at the opposed major surfaces, the plate mounting orifices of the group of plate mounting orifices arranged outside the second additional auxiliary spindle mounting area defined by the second group of the additional groups of auxiliary spindle mounting orifices; and
   a third group of the additional groups of auxiliary spindle mounting orifices define a perimeter of a third additional auxiliary spindle mounting area at the opposed major surfaces, the plate mounting orifices of the group of plate mounting orifices arranged outside the third additional auxiliary spindle mounting area defined by the third group of the additional groups of auxiliary spindle mounting orifices.

6. The mounting plate of claim 5, wherein the auxiliary orifice and the additional auxiliary orifices are radially located around the primary orifice.

7. The mounting plate of claim 5, wherein the auxiliary orifice and one of the additional auxiliary orifices are noncircular.

8. The mounting plate of claim 5, wherein two of the additional auxiliary orifices are circular and are opposed one another in a first direction, the auxiliary orifice and one of the additional auxiliary orifices are noncircular auxiliary orifices opposing one another in a second direction arranged 80° to 100° relative to the first direction.

9. The mounting plate of claim 1, wherein the auxiliary orifice is a non-circular orifice.

10. The mounting plate of claim 1, wherein the auxiliary orifice comprises a semi-annular perimeter.

11. The mounting plate of claim 1, wherein an area of the auxiliary orifice is at least 40% and less than 75% of the auxiliary spindle mounting area defined by the group of auxiliary spindle mounting orifices.

12. The mounting plate of claim 1, wherein the mounting plate further comprises an additional group of plate mounting orifices arranged in a rectangular pattern, the additional group of plate mounting orifices extending through the opposed major surfaces in the thickness direction, the additional group of plate mounting orifices defining a perimeter of an area at the opposed major surfaces.

13. A medical device suspension system, comprising:
   the mounting plate of claim 1;
   a primary spindle mounted to the mounting plate via the group of primary spindle mounting orifices such that an interior volume of the primary spindle is in fluid communication with the primary orifice; and
   an auxiliary spindle mounted to the mounting plate via the group of auxiliary spindle mounting orifices associated with the auxiliary orifice such that an interior volume of the auxiliary spindle is in fluid communication with the auxiliary orifice.

14. The medical device suspension system of claim 13, wherein:
   the mounting plate further comprises an additional auxiliary orifice extending through the opposed major surfaces in the thickness direction and an additional group of auxiliary spindle mounting orifices surrounding the additional auxiliary orifice and extending through the opposed major surfaces in the thickness direction, the additional group of auxiliary spindle mounting orifices defining a perimeter of an additional auxiliary spindle mounting area at the opposed major surfaces, the group of plate mounting orifices arranged outside the additional auxiliary spindle mounting area defined by the additional group of auxiliary spindle mounting orifices; and
   the medical device suspension system further comprises an additional auxiliary spindle mounted to the mounting plate via the additional group of auxiliary spindle mounting orifices associated with the additional auxiliary orifice such that an interior volume of the additional auxiliary spindle is in fluid communication with the additional auxiliary orifice.

15. A mounting plate for a medical device support system, comprising:
   opposed major surfaces spaced apart from one another in a thickness direction;
   a group of plate mounting orifices arranged in a regular hexagon pattern, the group of plate mounting orifices extending through the opposed major surfaces in the thickness direction and through the mounting plate to accommodate mounting hardware therethrough, the group of plate mounting orifices defining a perimeter of an area at the opposed major surfaces;
   a group of auxiliary spindle mounting orifices extending through the opposed major surfaces in the thickness direction and defining a perimeter of an auxiliary spindle mounting area at the opposed major surfaces, only one of the plate mounting orifices of the group of plate mounting orifices located within the auxiliary spindle mounting area defined by the group of auxiliary spindle mounting orifices; and an auxiliary orifice extending through the opposed major surfaces in the thickness direction and located within the auxiliary spindle mounting area defined by the group of auxiliary spindle mounting orifices;

wherein the mounting plate comprises three additional groups of auxiliary spindle mounting orifices extending through the opposed major surfaces, wherein:

a first group of the additional groups of auxiliary spindle mounting orifices define a perimeter of a first additional auxiliary spindle mounting area at the opposed major surfaces, another one of the plate mounting orifices of the group of plate mounting orifices located within the first additional auxiliary spindle mounting area defined by the first group of the additional groups of auxiliary spindle mounting orifices;

a second group of the additional groups of auxiliary spindle mounting orifices define a perimeter of a second additional auxiliary spindle mounting area at the opposed major surfaces, the plate mounting orifices of the group of plate mounting orifices arranged outside the second additional auxiliary spindle mounting area defined by the second group of the additional groups of auxiliary spindle mounting orifices; and a third group of the additional groups of auxiliary spindle mounting orifices define a perimeter of a third additional auxiliary spindle mounting area at the opposed major surfaces, the plate mounting orifices of the group of plate mounting orifices arranged outside the third additional auxiliary spindle mounting area defined by the third group of the additional groups of auxiliary spindle mounting orifices.

* * * * *